(12) United States Patent
MacDonald et al.

(10) Patent No.: US 8,283,313 B2
(45) Date of Patent: *Oct. 9, 2012

(54) METHODS OF INCREASING PLATELET AND HEMATOPOIETIC STEM CELL PRODUCTION

(75) Inventors: Brian R. MacDonald, Bryn Mawr, PA (US); Kenneth Kaushansky, Del Mar, CA (US)

(73) Assignee: Janssen Pharmaceutica, NV, Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 13/164,707

(22) Filed: Jun. 20, 2011

(65) Prior Publication Data

US 2011/0288019 A1     Nov. 24, 2011

Related U.S. Application Data

(62) Division of application No. 10/667,096, filed on Sep. 18, 2003, now Pat. No. 8,067,367.

(60) Provisional application No. 60/411,779, filed on Sep. 18, 2002, provisional application No. 60/411,700, filed on Sep. 18, 2002, provisional application No. 60/498,740, filed on Aug. 28, 2003.

(51) Int. Cl.
*A61K 38/02* (2006.01)

(52) U.S. Cl. ............. 514/7.8; 424/85.1; 424/198.1; 514/7.9; 530/300

(58) Field of Classification Search ............ None
See application file for complete search history.

(56) References Cited

U.S. PATENT DOCUMENTS

| | | |
|---|---|---|
| 3,654,090 A | 4/1972 | Wilhelmus et al. |
| 3,940,475 A | 2/1976 | Gross |
| 4,179,337 A | 12/1979 | Davis et al. |
| 4,301,144 A | 11/1981 | Iwashita et al. |
| 4,496,689 A | 1/1985 | Mitra |
| 4,563,303 A | 1/1986 | Ginnaga et al. |
| 4,612,132 A | 9/1986 | Wollenberg et al. |
| 4,640,835 A | 2/1987 | Shimizu et al. |
| 4,668,619 A | 5/1987 | Greenquist et al. |
| 4,670,417 A | 6/1987 | Iwasaki et al. |
| 4,784,589 A | 11/1988 | Robinson et al. |
| 4,791,192 A | 12/1988 | Nakagawa et al. |
| 4,997,915 A | 3/1991 | Tan et al. |
| 5,141,851 A | 8/1992 | Brown et al. |
| 5,143,854 A | 9/1992 | Pirrung et al. |
| 5,198,424 A | 3/1993 | McEver |
| 5,270,170 A | 12/1993 | Schatz et al. |
| 5,326,558 A | 7/1994 | Turner et al. |
| 5,338,665 A | 8/1994 | Schatz et al. |
| 5,358,934 A | 10/1994 | Borovsky et al. |
| 5,359,115 A | 10/1994 | Campbell et al. |
| 5,384,331 A | 1/1995 | Kogan et al. |
| 5,411,942 A | 5/1995 | Widmer et al. |
| 5,420,328 A | 5/1995 | Campbell |
| 5,424,186 A | 6/1995 | Fodor et al. |
| 5,432,018 A | 7/1995 | Dower et al. |
| 5,639,603 A | 6/1997 | Dower et al. |
| 5,672,662 A | 9/1997 | Harris et al. |
| 5,723,286 A | 3/1998 | Dower et al. |
| 5,770,358 A | 6/1998 | Dower et al. |
| 5,869,451 A * | 2/1999 | Dower et al. .............. 514/7.8 |
| 5,891,912 A | 4/1999 | Kawashima et al. |
| 5,932,546 A | 8/1999 | Barrett et al. |
| 5,989,833 A | 11/1999 | Charon et al. |
| 6,013,067 A | 1/2000 | Fibbe et al. |
| 6,060,052 A | 5/2000 | Murray et al. |
| 6,083,913 A | 7/2000 | Dower et al. |
| 6,121,238 A | 9/2000 | Dower et al. |
| 6,251,864 B1 | 6/2001 | Dower et al. |
| 6,465,430 B1 | 10/2002 | Dower et al. |
| 6,506,362 B1 | 1/2003 | Dower et al. |
| 6,835,809 B1 * | 12/2004 | Liu et al. .................. 530/324 |
| 7,091,311 B2 | 8/2006 | Dower et al. |
| 7,189,827 B2 | 3/2007 | Feige |
| 7,576,056 B2 * | 8/2009 | MacDonald et al. ........ 514/1.1 |
| 7,615,533 B2 * | 11/2009 | Yurkow et al. ............. 514/1.1 |
| 7,723,295 B2 * | 5/2010 | MacDonald et al. ........ 514/7.8 |
| 2002/0187124 A1 | 12/2002 | Takahashi |
| 2003/0158116 A1 | 8/2003 | Dower et al. |
| 2004/0028649 A1 | 2/2004 | Gianni |
| 2005/0137133 A1 * | 6/2005 | MacDonald et al. ........ 514/12 |
| 2005/0282277 A1 | 12/2005 | MacDonald et al. |
| 2006/0040866 A1 | 2/2006 | MacDonald et al. |
| 2006/0058240 A1 | 3/2006 | Dower et al. |
| 2006/0210542 A1 | 9/2006 | Yurkow et al. |
| 2007/0148091 A1 | 6/2007 | Dower et al. |
| 2008/0119384 A1 | 5/2008 | Yurkow et al. |
| 2009/0214489 A1 | 8/2009 | Dower et al. |

FOREIGN PATENT DOCUMENTS

EP     0 450 715 A1     10/1991
(Continued)

OTHER PUBLICATIONS

Cwirla et al. Peptide agonist of the thrombopoietic receptor as potent as the natural cytokine. Science 276: 1696-1699, 1997.* Dower et al. Peptide agonists of the thrombopoietin receptor. Stem Cells 16(Suppl 2): 21-29, 1998.*
Wendling, F. Thrombopoietin: its role from early hematopoiesis to platelet production. Haematol 84: 158-166, 1999.*
Kuter et al. Recombinant human thrombopoietin: basic biology and evaluation of clinical studies. Blood 100: 3457-3469, 2002.*
De Serres et al. Pharmacokinetics and hematological effects of the PEGylated thrombopoietin peptide mimetic GW395058 in rats and monkeys after intravenous or subcutaneous administration. Stem Cells 17: 316-326, 1999.*
Fox et al. Thrombopoietin expands hematopoietic stem cells after transplantation J Clin Invest 110(3): 389-394, 2002.*
In the U. S. Patent and Trademark Office U.S. Appl. No. 10/083,768 Non-Final Office Action dated Feb. 25, 2005, 8 pages.
In the U. S. Patent and Trademark Office U.S. Appl. No. 10/667,096 *Ex Parte Quayle* Action dated Mar. 23, 2010, 5 pages.
In the U. S. Patent and Trademark Office U.S. Appl. No. 10/667,096 Final Office Action dated Apr. 7, 2009, 10 pages.
In the U. S. Patent and Trademark Office U.S. Appl. No. 10/667,096 Final Office Action dated May 8, 2007, 11 pages.
In the U. S. Patent and Trademark Office U.S. Appl. No. 10/667,096 Non-Final Office Action dated Aug. 12, 2009, 7 pages.

(Continued)

*Primary Examiner* — Bridget E Bunner
(74) *Attorney, Agent, or Firm* — Venable LLP

(57) ABSTRACT

A method of increasing hematopoietic stem cell production is disclosed. The method includes administering a TPO mimetic compound to a subject. Pharmaceutical compositions including a TPO mimetic compound and a pharmaceutically acceptable carrier are also disclosed.

9 Claims, 2 Drawing Sheets

FOREIGN PATENT DOCUMENTS

| | | |
|---|---|---|
| EP | 0 613 683 A1 | 9/1994 |
| EP | 0 668 352 A1 | 8/1995 |
| EP | 0 675 201 A1 | 10/1995 |
| EP | 0 690 127 A1 | 1/1996 |
| EP | 0 783 003 A1 | 7/1997 |
| GB | 2 186 579 A | 8/1987 |
| GB | 2 285 446 A | 7/1995 |
| WO | WO-90/15070 A1 | 12/1990 |
| WO | WO-91/07988 A1 | 6/1991 |
| WO | WO-91/08752 A1 | 6/1991 |
| WO | WO-93/25221 A1 | 12/1993 |
| WO | WO-94/17784 A1 | 8/1994 |
| WO | WO-95/05843 A1 | 3/1995 |
| WO | WO-95/11922 A1 | 5/1995 |
| WO | WO-95/18858 A1 | 7/1995 |
| WO | WO-95/21626 A1 | 8/1995 |
| WO | WO-95/21919 A2 | 8/1995 |
| WO | WO-95/21920 A1 | 8/1995 |
| WO | WO-95/28907 A2 | 11/1995 |
| WO | WO-95/34326 A1 | 12/1995 |
| WO | WO-96/14293 A1 | 5/1996 |
| WO | WO-96/17062 A1 | 6/1996 |
| WO | WO-96/17067 A1 | 6/1996 |
| WO | WO-96/34016 A1 | 10/1996 |
| WO | WO-96/40189 A1 | 12/1996 |
| WO | WO-96/40750 A1 | 12/1996 |
| WO | WO-9825965 A2 * | 6/1998 |
| WO | WO-01/21180 A1 | 3/2001 |
| WO | WO-02/051861 A2 | 7/2002 |
| WO | WO-02/078612 A2 | 10/2002 |
| WO | WO-2004/026332 A1 | 4/2004 |
| WO | WO-2005/023834 A2 | 3/2005 |

OTHER PUBLICATIONS

In the U. S. Patent and Trademark Office U.S. Appl. No. 10/667,096 Non-Final Office Action dated Aug. 3, 2006, 10 pages.
In the U. S. Patent and Trademark Office U.S. Appl. No. 10/667,096 Non-Final Office Action dated Oct. 8, 2008, 8 pages.
In the U. S. Patent and Trademark Office U.S. Appl. No. 10/918,561 Ex Parte Quayle Action dated Sep. 4, 2008, 7 pages.
In the U. S. Patent and Trademark Office U.S. Appl. No. 10/918,561 Non-Final Office Action dated Mar. 30, 2007, 11 pages.
In the U. S. Patent and Trademark Office U.S. Appl. No. 10/918,561 Non-Final Office Action dated Nov. 27, 2007, 21 pages.
In the U. S. Patent and Trademark Office U.S. Appl. No. 11/181,049 Non-Final Office Action dated May 21, 2007, 15 pages.
In the U. S. Patent and Trademark Office U.S. Appl. No. 11/200,416 Non-Final Office Action dated Jan. 7, 2009, 27 pages.
In the U. S. Patent and Trademark Office U.S. Appl. No. 11/254,419 Non-Final Office Action dated Jun. 27, 2006, 6 pages.
In the U. S. Patent and Trademark Office U.S. Appl. No. 11/354,065 Non-Final Office Action dated Jul. 22, 2008, 28 pages.
In the U. S. Patent and Trademark Office U.S. Appl. No. 11/610,226 Final Office Action dated Apr. 29, 2010, 22 pages.
In the U. S. Patent and Trademark Office U.S. Appl. No. 11/610,226 Non-Final Office Action dated Jun. 2, 2011, 17 pages.
In the U. S. Patent and Trademark Office U.S. Appl. No. 11/610,226 Non-Final Office Action dated Sep. 25, 2009, 19 pages.
In the U. S. Patent and Trademark Office U.S. Appl. No. 11/818,049 Non-Final Office Action dated Feb. 18, 2009, 11 pages.
In the U. S. Patent and Trademark Office U.S. Appl. No. 12/103,377 Final Office Action dated Dec. 13, 2010, 15 pages.
In the U. S. Patent and Trademark Office U.S. Appl. No. 12/103,377 Non-Final Office Action dated Jun. 24, 2011, 13 pages.
In the U. S. Patent and Trademark Office U.S. Appl. No. 12/103,377 Non-Final Office Action dated Jun. 7, 2010, 11 pages.
Ballmaier et al., "C-Mpl Mutations are the Cause of Congenital Amegakaryocytic Thrombocytopenia," *Blood*, 2001; 97:139-146.
Barker et al., "Cyclic RGE Peptide Analogues as Antiplatelet Antithrombotics," *J. Med. Chem.*, 1992; 35:2040-2048.
Bartley et al., "Identification and Cloning of a Megakaryocyte Growth and Development Factor that is a Ligand for the Cytokine Receptor Mpl," *Cell*, 1994; 77:1117-1124.

Basser et al., "Randomized, Blinded, Placebo-Controlled Phase I Trail of Pegylated Recombinant Human Megakaryocyte Growth and Development Factor with Filgrastim after Dose-Intensive Chemotherapy in Patients with Advanced Cancer," *Blood*, 1997; 89(9):3118-3128.
Baynes et al., "Bone Marrow and Peripheral Blood Hematopoietic Stem Cell Transplantation: Focus on Autografting," *Clinical Chemistry*, 2000; 46(8B):1239-1251.
Bazan et al., "Structural Design and Molecular Evolution of a Cytokine Receptor Superfamily," *Proc. Natl. Acad. Sci.*, 1990; 87:6934-6938.
Berger et al., "A New Method for the Synthesis of Optically Active α-Amino Acids and Their $N^\alpha$ Derivatives via Acylamino Malonates," *J. Org. Chem.*, 1973; 38(3):457-460.
Bhatia et al., "Purification of Primitive Human Hematopoietic Cells Capable of Repopulating Immune-Deficient Mice," *PNAS*, 1997; 94:5320-5325.
Bonnet et al., "Cytokine Treatment or Accessory Cells are Required to Initiate Engraftment of Purified Primitive Human Hematopoietic Cells Transplanted at Limiting Doses into NOD/SCID Mice," *Bone Marrow Transplanation*, 1999; 23:203-209.
Broxmeyer et al., "Colony Assays of Hematopoietic Progenitor Cells and Correlations to Clinical Situations," *CRC Critical Review-Oncology/Hematology*, 1983; 1:227-257.
Cain et al., "Myasthenia Gravis and Polymyositis in a Dog Following Fetal Hematopoietic Cell Transplantation *Transplantation*," 1986; 41(1):21-25.
Caras et al., "Signal Peptide for Protein Secretion Directing Glycophospholipid Membrane Anchor Attachment," *Science*, 1989; 243:1196-1198.
Case et al., "The Pharmacokinetics and Pharmacodynamics of GW395058, a Peptide Agonist of the Thrombopoietin Receptor, in the Dog, a Large-Animal Model of Chemotherapy-Induced Thrombocytopenia," *Stem Cells*, 2000; 18:360-365.
Cho et al.,"An Unnatural Biopolymer," *Science*, 1993; 261:1303-1305.
Cwirla et al., "Peptides on Phage: A Vast Library of Peptides for Identifying Ligands," *Proc. Natl. Acad. Sci.*, 1990; 87:6378-6382.
Daumas et al., "Gramicidin A Analogs: Influence of the Substitution of the Tryptophans by Naphthylalanines," *Biochimie*, 1989; 71:77-81.
De Sauvage et al., "Stimulation of Megakaryoctyopoiesis and Thrombopoiesis by the cMpl Ligand," *Nature*, 1994; 369:533-538.
De Serres et al., "Immunogenicity of Thrombopoietin Mimetic Peptide GW395058 in BALB/c Mice and New Zealand White Rabbits: Evaluation of the Potential for Thrombopoietin Neutralizing Antibody Production in Man," *Stem Cells*, 1999; 17:203-209.
Dexter et al., "Growth Factor-Dependent Hemopoietic Precursors Cell Lines," *J. Exp. Med.*, 1980; 152:1036-1047.
Dower et al., "High Efficiency Transformation of *Ecoli* by High Voltage Electroporation," *Nucleic Acids Research*, 1988; 16(13):6127-6145.
Dower et al., "The Search for Molecular Diversity (II): Recombinant and Synthetic Randomized Peptide Libraries," *Ann. Rep. Med. Chem.*, 1991; 26:271-280.
Evans et al., "Design of Nonpeptidal Ligands for a Peptide Receptor: Cholecystokinin Antagonists," *J. Med. Chem*, 1987; 30(7):1229-1239.
Fauchere et al., "Elements for the Rational Design of Peptide Drugs," *Adv. Drug Res.*, 1986; 15:29-69.
Fibbe et al., "Accelerated Reconstitution of Platelets and Erythrocytes after Syngeneic Transplantation of Bone Morrow Cells Derived from Thrombopoietin Pretreated Donor Mice," *Blood*, 1995; 86(9):3308-3313.
Filshie, "Cytokines in Haemopoietic Progenitor Mobilisation for Peripheral Blood Stem Cell Transplantation," *Current Pharmaceutical Design*, 2002; 8:379-394.
Fodor et al., "Light-Directed, Spatially addressable Parallel Chemical Synthesis," *Science*, 1991; 251:767-773.
Gallacher et al., "Isolation and Characterization of Human $CD34^-Lin^-$ and $CD34^+Lin^-$ Hematopoietic Stem Cells using Cell Surface Markers AC133 and CD7," *Blood*, 2000; 95(9):2813-2820.

Gante, "Peptidomimetics-Tailored Enzyme Inhibitors," *Angen. Chem. Int. Ed. Engl.*, 1994; 33:1699-1720.

Gisin, "The Preparation of Merrifield-Resins Through Total Esterification with Cesium Salts," *Helv. Chim. Acta.*, 1973; 56(143):1476-1482.

Goldman et al, "Haematological Reconstitution After Autografting for Chronic Granulocytic Leukaemia in Transformation: The Influence of Previous Splenectomy," *Br. J. Haematol.*, 1980; 45:223-231.

Good et al., "Bone Marrow Transplantation—An Expanding Approach to Treatment of Many Diseases," *Cellular Immunol.*, 1983; 82:36-54.

Gurney et al., "Genomic Structure, Chromosomal Localization, and Conserved Alternative Splice Forms of Thrombopoietin," *Blood*, 1995; 85(4):981-988.

Hann et al., "On the Double Bond Isostere of the Peptide Bond: Preparation of an Enkephalin Analogue," *J. Chem. Soc. Perkin Trans.*, 1982; 307-314.

Harker et al., "Kinetics of Thrombopoiesis," *J. Clin. Invest.*, 1968; 47:458-465.

Hershko et al., "Cure of Aplastic Anaemia in Paroxysmal Nocturnal Haemoglobinuria by Marrow Transfusion from Identifical Twin: Failure of Peripheral-Leucocyte Transfusion to Correct Marrow Aplasia," *The Lancet*, 1979; 945-947.

Hession et al., "Endothelial Leukocyte Adhesion Molecule 1: Direct Expression Cloning and Functional Interactions," *Proc. Acad. Sci. USA*, 1990; 87:1673-1677.

Hirokawa et al., "Restoration of Impaired Immune Functions in Aging Animals," *Clin. Immunolo. Immunopathol*, 1982; 22:297-304.

Holladay et al., "Synthesis of Hydroxyethylene and Ketomethylene Dipeptide Isosteres," *Tetrahedron Letter*, 1983; 24:4401-4404.

Horvath et al., Synthesis and Biological Activity of LH-RH Antagonists Modified in Position 1, *Peptides*, 1982; 3:969-971.

Hruby et al., "Emerging approaches in the molecular design of receptor-selective peptide ligands: conformational, topographical and dynamic considerations," *Biochem J.*, 1990; 268:249-262.

Hruby, Victor J., "Conformational Restrictions of Biologically Active Peptides Via Amino Acid Side Chain Groups," *Life Sci.*, Pergamon Press, 1982; 31:189-199.

Hudson et al., "Methionine Enkephalin and Isosteric Analogues," *Int. J. Pept. Prot. Res.*, 1979; 14:177-185.

International Search Report from PCT/US2003/029701 dated Mar. 3, 2004.

International Search Report from PCT/US2006/005322 dated Apr. 26, 2007.

International Search Report from PCT/US2006/030359 dated Mar. 15, 2007.

Jennings-White et al., "Synthesis of Ketomethylene Analogs of Dipeptides," *Tetrahedron Letters*, 1982; 23:2533-2534.

Kato et al., "Purification and Characterization of Thrombopoietin," *J. Biochem*, 1995; 118:229-236.

Kaushansky et al., "Promotion of Megakaryocyte Progenitor Expansion and Differentiation by the c-Mpl Ligand Thrombopoietin," *Nature*, 1994; 369:568-571.

Kaushansky et al., "Thrombopoietin Expands Erythroid Progenitors, Increases Red Cell Production, and Enhances Erythroid Recovery after Myelosuppressive Therapy," *J. Clin. Invest.*, 1995; 96:1683-1687.

Kaushansky et al., "Thrombopoietin Expands Erythroid, Granulocyte-Macrophage, and Megakaryocytic Progenitor Cells in Normal and Myelosuppressed Mice," *Exp. Hematol.*, 1996; 24:265-269.

Kaushansky, "Hematopoietic Growth Factor Mimetics," *Annals of the New York Academy of Sciences*, 2001; 938:131-138.

Kaushansky, "Thrombopoietin: accumulating evidence for an important biological effect on the hematopoietic Stem Cell," *Annals of the New York Academy of Sciences*, 2003; 996:39-43. (Abstract).

Kimura et al., "Hematopoietic Stem cell Deficiencies in Mice Lacking c-Mpl, the Receptor for Thrombopoietin," *Proc. Natl. Acad. Sci.*, 1998; 95:1195-1200.

Kojima et al., "Molecular Cloning and Expression of Megakaryocyte Potentiating Factor cDNA," *J. Biol. Chem.*, 1995; 21984-21990.

Korbling et al., "Autologous Transplantation of Blood-Derived Hemopoietic Stem Cells After Myeloablative Therapy in a Patient with Burkitt's Lymphoma," *Blood*, 1986; 67:529-532.

Ku et al., "Thrombopoietin, the Ligand for the Mpl Receptor, Synergizes with Steel Factor and Other Early Acting Cytokines in Supporting Proliferation of Primitive Hematopoietic Progenitors of Mice," *Blood*, 1996; 87(11):4544-4551.

Kuter et al., "The Purification of Megapoietin: A Physiological Regulator of Megakaryocyte Growth and Platelet Production," *Proc. Natl. Acad. Sci.*, 1994; 91:11104-11108.

Lajtha, L. G., "Haemopoietic Stem Cells: Concepts and Definitions," *Blood Cells*, 1979; 5:447-455.

Lajtha, L. G., "Stem Cell Concepts," *Differentiation*, 1979; 14:23-34.

Lin et al., "Expression of T Cell Antigen Receptor Heterodimers in a Lipid-Linked Form," *Science Reports*, 1990; 249:677-679.

Luthman et al., "Peptides and Peptidomimetics," *A Textbook of Drug Design and Development*, 2nd Edition, Harwood Academic Publishers GmbH, 1996; 14:386-406.

McDonald et al., "Thrombopoietin—It's Biology, Clinical Aspects and Possibilities," *Am. J. Pediatric Hematology/Oncology*, 1992; 14:8-21.

Merrifield, "Solid Phase Peptide Synthesis. I. The Synthesis of a Tetrapeptide," *J. Am. Chem. Soc.*, 1963; 85:2149-2154.

Metcalf et al., "Thrombopoietin—At Last," *Nature*, 1994; 369:519-520.

Methia et al., "Oligodeoxynucleotides Antisense to the Proto-Oncogene c-mp1 Specifically Inhibit In Vitro Megakaryocytopoiesis," *Blood*, 1993; 82(5):1395-1401.

Monfardini et al., "A Branched Monomethoxypoly(ethylene glycol) for Protein Modification," *Bioconjugate Chem.*, 1995; 6:62-69.

Morgan et al., "Approaches to the Discovery of Non-Peptide Ligands for Peptide Receptors and Peptidases," *Ann. Rep. Med. Chem.*, 1989; 24:243-252.

Morley, "Modulation of the Action of Regulatory Peptides by Structural Modification," *Trends in Pharm Sci.*, 1980; 463-468.

Mosmann, "Rapid Colorimetric Assays for Cellular Growth and Survival: Application to Proliferation and Cytotoxicity Assays," *J. Immunol. Methods*, 1983; 65:55-63.

Neelis et al., "Prevention of Thrombocytopenia by Thrombopoietin in Myelosuppressed Rhesus Monkeys Accompanied by Prominent Erythropoietic Stimulation and Iron Depletion," *Blood*, 1997; 90(1):58-63.

Nestor et al., "Synthesis and Biological Activity of Some Very Hydrophobic Superagonist Analogues of Luteinizing Hormone-Releasing Hormone," *J. Med. Chem.*, 1982; 25:795-801.

Nothdurft et al., "Studies on the Regeneration of the CFU-C Population in Blood and Bone Marrow of Lethaly Irradiated Dogs After Autologous Transfusion of Cryopreserved Mononuclear Blood Cells," *Scand. J. Haematol.*, 1977; 19:470-481.

Ochs et al., "952 Immune Reconstitution in Adenosine Deaminase Deficient Severe Combined Immune Deficiency," *Pediatr. Res.*, 1981; 15(4):601.

Or et al., "Cysteine Alkylation in Unprotected Peptides: Synthesis of a Carbavasopressin Analogue by Intramolecular Cysteine Alkylation," *J. Org. Chem.*, 1991; 56:3146-21-49.

Paige et al., "Precursors of Murine B Lymphocytes," *J. Exp. Med.*, 1981; 153:154-165.

Papayannopoulou et al., "Insights into the Cellular Mechanisms of Erythropoietin-Thrombopoietin Synergy," *Experimental Hematology*, 1996; 24:660-669.

Pietta et al., "Amide Protection and Amide Supports in Solid-Phase Peptide Synthesis," *Chem. Commn.*, 1970; 650-651.

Porter et al., "Synthesis, Resolution and Characterization of Ring Substituted Phenylalanines and Tryptophans," *Int. J. Peptide Protein Res.*, 1987; 30(1) (Abstract).

Prochazka et al., "The 1- and 2-Naphtylalanine Analogs of Oxytocin and Vasopressin," *Collect. Czech. Chem. Commun.*, 1995; 60:2170-2177.

Prummer et al., "Recovery of Immune Functions in Dogs After Total Body Irradiation and Transplantation of Autologous Blood or Bone Marrow Cells," *Exp. Hematol.*, 1985; 13:891-898.

Ragharachar et al., "Comparison of the Repopulating Potential of Stem Cells Derived from Blood and Bone Marrow: Autotransplants in Dogs," *J. Cell. Biochem. Suppl.*, 1983; Poster Session 0198:78.

Reiffers et al., "Successful Autologous Transplantation With Peripheral Blood Hemopoietic Cells in a Patient With Acute Leukemia," *Exp. Hematol.*, 1986; 14:312-315.

Renschler et al., "Synthetic Peptide Ligands of the Antigen Binding Receptor Induce Programmed Cell Death in a Human B-Cell Lymphoma," *Immunology*, 1994; 91:3623-3627.

Roberts et al., "Unusual Amino/Acids in Peptide Synthesis," *The Peptides*, Academic Press, 1983; 5(Chapter 6):341-449.

Sarpel et al., "The Collection, Preservation and Function of Peripheral Blood Hematopoietic Cells in Dogs," *Exp. Hematol.*, 1979; 7(2):113-120.

Singer et al., "Pegylated Thrombopoietin (TPO)-Mimetic Peptides Bind Human to TPO Receptor Causing Proliferation and Maturation of Megakaryocytes In Vitro," 1998; Abstract #2336(Poster Board Session # 193-IV):568A.

Sitnicka et al., "The Effect of Thrombopoietin on the Proliferation and Differentiation of Murine Hematopoietic Stem Cells," *Blood*, 1998; 87(12):4998-5005.

Solar et al., "Role of C-Mpl in Early Hematopoiesis," *Blood*, 1998; 92:4-10.

Somlo et al., "Recombinant Human Thrombopoietin in Combination with Granulocyte Colony-Stimulating Factor Enhances Mobilization of Peripheral Blood Progenitor Cells, Increases Peripheral Blood Platelet Concentration, and Accelerates Hematopoietic Recovery Following High0Dose Chemotherapy," *Blood*, 1999; 93(9):2798-2806.

Souyri et al. "A Putative Truncated Cytokine Receptor Gene Transduced by the Myeloproliferative Leukemia Virus Immortalizes Hematopoietic Progenitors," *Cell*, 1990; 63:1137-1147.

Spatola et al., "Structure-Activity Relationships of Enkephalins Containing Serially Replaced Thiomethylene Amide Bond Surrogates," *Live Sci.*, 1986; 38:1243-1249.

Spatola et al., Chemistry and Biochemistry of Amino Acids, Peptides, and Proteins, B Weinstein, eds., Marcel Dekker, New York, 1983; 267-356. et al.

Spertini et al., "Regulation of Leukocyte Migration by Activation of the Leukocyate Adhesion Molecule-1 (LAM-1) Selectin," *Nature*, 1991; 349:691-694.

Tice et al., "Parenteral Drug Delivery: Injectables," *Treaties on Controlled Drug Delivery*, Ed., Marcel Dekker, New York, 1992; 315-339.

Tichelli et al., "Repeated Peripheral Stem Cell Mobilization in Healthy Donors: Time-Dependent Changes in Mobilization Efficiency," *Br. J. Hematol*, 1999; 106:152-158.

Tilly et al., "Haemopoietic Reconstitution After Autologous Peripheral Blood Stem Cell Transplantation in Acute Leukaemia," *The Lancet*, 1986; 328(8499):154-155.

To et al., "Peripheral Blood Stem Cell Autografting: A New Therapeutic Option for AML?" *Brit. J. Haematol.*, 1987; 66:285-288.

Tulunay et al., "Protection of Lethally Irradiated Mice with Allogeneic Fetal Liver Cells: Influence of Irradiation Dose on Immunologic Reconstitution," *Proc. Nat. Acad. Set.*, 1975; 72(10):4100-4104.

Verber et al., "The Design of Metabolically-stable Peptide Analogs," *Trends in Neurosciences (TINS)*, 1990; 392-396.

Vickery et al., "Effect of Immune Reconstitution on Resistance to *Brugia pahangi* in Congenitally Athymic Nude Mice," *J. Parasitol*, 1983; 69(3):478-485.

Vigon et al., "Molecular Cloning and Characterization of MPL, the Human Hormology of the v-mpl Oncogene: Identification of a Member of the Hematopoietic Growth Factor Receptor Superfamily," *Proc. Natl. Acad. Sci.*, 1992; 89:5640-5644.

Wada et al., "Characterization of the Truncated Thrombopoietin Variants," *Biosphysical Research Communications*, 1995; 213:1091-1098.

Wang et al., "Design and Synthesis of Novel $X^2$-Constrained Phenylanine, Naphthylalanine, and Tryptophan Analogues and Their use in Biologically Active Melanotropin Peptides," *Tetrahedron*, 2002; 58:7365-7374.

Wang et al., "Primitive Human Hematopoietic Cells are Enriched in Cord Blood Compared with Adult Bone Marrow or Mobilized Peripheral Blood as Measured by the Quantitative In Vivo SCID-repopulating Cell Assay," *Blood*, 1997; 89:3919-3924.

Weaner et al., "Tritium Labeling of N-Protected Amino Acids and Peptides Containing O-Alkyl-Tyrosyl Residues," *Synthesis and Applications of Isotopically Labelled Compounds*, 1994; 137-140.

Wendling et al., "c-Mpl Ligand is a Humoral Regulator of Megakaryocytopoisis," *Nature*, 1994; 369:571-574.

Wendling et al., "The Oncongene V-MPL: A Putative Truncated Cytokine Receptor which Immortalizes Hematopoietic Progenitors," *Nouv Rev Fr Hematol*, 1991; 33(2)145-146.

Wrighton et al., "Small Peptide Mimetics of Erythropoietin," *Blood, Suppl 1*, 1996; 88(10):543a, Abstract 2160.

Wrighton et al., "Small Peptides as Potent Mimetics of the Protein Hormone Erythropoietin," *Science*, 1996; 273:458-463.

Yabe et al., "Analogues of Luteinizing Hormone-Releasing Hormone with Modification in Position 31)," *Chem. Pharm. Bull.*, 1976; 3149-3157.

Yabe et al., "Synthesis and Biological Activity of Somatostatin Analogues Modified at the Tryptophan Residue," *Chem. Pharm. Bull*, 1978; 26(3):993-997.

Yabe et al., "Synthesis and Biological Activity of Tetragastrin Analogues Modifying the Tryptophan Residue," *Chame. Pharm. Bull.*, 1977; 25(10):2731-2734.

Zalipsky et al., "Functionalized Poly(ethylene glycol) for Preparation of Biologically Relevant Conjugates," *Bioconjugate Chem.*, 1995; 6:150-165.

\* cited by examiner

Figure 2 – PRIOR ART

METHODS OF INCREASING PLATELET AND HEMATOPOIETIC STEM CELL PRODUCTION

CROSS-REFERENCE TO RELATED APPLICATIONS

This application is a divisional application of U.S. application Ser. No. 10/667,096, filed Sep. 18, 2003, now U.S. Pat. No. 8,067,367, issued Nov. 29, 2011, which in turn claims priority to Application Nos. 60/411,779 and 60/411,700 filed on Sep. 18, 2002, and Application No. 60/498,740, filed Aug. 28, 2003, the entire contents of which are incorporated by reference in their entireties.

BACKGROUND OF THE INVENTION

Thrombopoietin (TPO), initially cloned as a major regulator of platelet production, plays a pivotal role in hematopoietic stem cell (HSC) biology. Kaushansky et al., Nature, 369:568-571 (1994). Virtually all primitive HSC that display repopulating activity express c-Mpl, the receptor of TPO. Solar et al., Blood, 92:4-10 (1998). TPO alone or in combination with other early acting cytokines, such as stem cell factor (SCF), interleukin 3 (IL-3), or Flt-3 ligand enhance proliferation of primative HSC in vitro. Ku et al., Blood, 87:4544-4551 (1996); Sitnicka et al., Blood, 87:4998-5005 (1996). In vivo studies have confirmed these conclusions. Kimura et al., Proc. Natl. Acad. Sci. U.S.A., 95:1195-1200 (1998). The importance of TPO in stem cell self renewal and expansion was also supported by the clinical observation that mutations of the c-Mpl gene caused congenital amegakaryocytic thrombocytopenia, a disease in which all hematopoietic lineages fail during childhood. Ballmaier et al., Blood, 97:139-146 (2001). It has been found that expansion of HSCs in adult bone marrow is 10 to 20 times less robust in tpo−/− mice following bone marrow transplantation. Exogenously added TPO rescued this defect. Fox et al., J. Clin. Invest., 110:389-394 (2002). These reports indicate that TPO is a major non redundant contributor to self renewal and expansion of HSCs.

Autologous stem cell transplantation (ASCT) is increasingly widely used as a means of reconstituting the bone marrow following the administration of potentially curative, myeloablative, high dose chemotherapy. The basis for this technique is to mobilize HSCs from bone marrow to peripheral blood (using G-CSF+/−priming chemotherapy) from which they are harvested by apheresis. These stem cells, which form a minority of the harvested population, are then capable of reconstituting the bone marrow when reinfused following myeloablative therapy. Stem cells obtained from peripheral blood in this technique appear to be similar to cord blood cells and superior to bone marrow cells in their ability to regenerate bone marrow following myeloablative therapy with time to neutrophil and platelet engraftment of less than 10 days. The most common tumor types in which ASCT is used are myeloma, lymphoma (both Hodgkins Disease and Non-Hodgkins Lymphoma) and Acute Myeloid Leukemia. High dose chemotherapy with ASCT may be increasingly used as first line therapy, particularly in myeloma, but it is also used as salvage therapy following the failure of first line chemotherapy. Such subjects often have been heavily pretreated and thus have bone marrow with impaired hematopoietic potential.

Following the re-infusion of these harvested cells into the subject, there is a period of time during which the subject, e.g., a human patient, is at risk of infection (low neutrophils) and bleeding (low platelets). This period of time varies depending on the number of re-infused stem cells, which in turn depends on the ability to stimulate the expansion of stem cells from bone marrow. Further, some subjects also develop bone marrow failure after an initial period of engraftment.

Stem cell transplantation is also used in an allogeneic setting when peripheral blood stem cells are mobilized and harvested from HLA matched donors. Such allogeneic transplants are less frequently employed than ASCT because of the incidence of graft versus host disease but may be used when it is not possible to obtain sufficient stem cells from the patient. However the use of allogeneic stem cells to obtain partial engraftment in the absence of complete myeloablation (the 'mini transplant') may also offer some therapeutic benefit due to a graft versus tumor effect. Another possible use, currently in an extremely small number of patients is in the field of gene therapy where normal allogeneic bone marrow cells or autologous cells transduced with a normal copy of a defective gene may be curative for some inherited disease caused by single gene defects. Allogeneic transplants are also under investigation as a therapeutic option for autoimmune diseases.

Despite the potential utility and simplicity of ASCT, there are significant limitations to its widespread use beyond the expected period of pancytopenia, for which intensive subject support is required to allow the re-infused cells to resume levels of hematopoiesis sufficient to maintain peripheral blood counts. A significant proportion (up to 40%) of transplanted subjects requires prolonged platelet transfusions following transplant (primary failure of engraftment). A smaller group (5-10% in autologous but >20% with allogeneic transplant) develop secondary thrombocytopenia despite initial engraftment, sometimes requiring prolonged transfusions. Failure of engraftment or delayed engraftment is associated with increased mortality, increased healthcare costs and decreased subject quality of life.

There thus exists a need to increase HSC production in such subjects. Studies have demonstrated that administration of TPO to patients results in mobilization of peripheral blood progenitor cells. One study demonstrated the mobilization of colony forming cells from multiple lineages and CD34+ cells into the peripheral blood following multiple dose administration of TPO in combination with G-CSF. Another study identified a 6 fold increase in circulating CD34+ cells 3-7 days after administration of a single dose of TPO in cancer patients with otherwise normal hematopoiesis. In this study, a stem cell enriched subfraction (CD34+Thy+Lin−) was increased nearly 9 fold and the committed megakaryocytic subfraction (CD34+CD41+CD14−) was increased nearly 15 fold. This study suggests that TPO is capable of mobilizing both self-renewing HSC and committed daughter cells from bone marrow. Although the availability of recombinant TPO (rhTPO) has shown promise in increasing HSC production, a need exists for an improvement in TPO therapy by way of the mode of drug delivery There thus exists a need for small molecule mimetic compounds of TPO that retain substantially the full agonist activity of TPO, while at the same time permitting various modes of administration.

There also exists a need for small molecule mimetic compounds of TPO having reduced immunogenicity relative to one or more of rhTPO and rhIL-11 as well as improved pharmacokinetic profile relative to one or more of rhTPO and rhIL-11.

SUMMARY OF THE INVENTION

The present invention is directed to a method of increasing HSC production in a subject comprising a step of administering a TPO mimetic compound to the subject. The TPO mimetic compound may be administered to the subject alone or in a pharmaceutically acceptable carrier. The TPO mimetic compound can be employed alone or can be combined with one or more additional TPO mimetic compounds and/or other agents that can enhance stem cell mobilization from bone marrow, including, e.g., G-CSF, SCF, IL-3 and/or Flt-3.

The present invention is thus also directed to a TPO mimetic pharmaceutical composition that comprises an effective amount of a TPO mimetic compound and a pharmaceutically acceptable carrier. An effective amount of a TPO mimetic compound is present when upon administration the TPO mimetic compound enhances expansion of the stem cell population within bone marrow of a subject and/or mobilizes the stem cells into the peripheral circulation of a subject.

The present invention is also directed to a method of providing HSCs to a subject. The method can include the steps of administering a TPO mimetic compound to the subject to enhance expansion of the stem cell population within bone marrow and/or to mobilize the stem cells into the peripheral circulation. Next, the method can include harvesting one or more stem cells from the subject from either the bone marrow or from the peripheral circulation and then transplanting the harvested one or more stem cells into the subject.

The present invention is also directed to a method of providing HSCs from a donor subject to a recipient subject.

BRIEF DESCRIPTION OF THE DRAWINGS

FIG. 2 is a listing of compounds, which can be suitable for use in the method of the present invention. (Left Column: SEQ ID NOS: 1-4, 1, 2, and 5-12; middle column: SEQ ID NOS: 13-17, 17, and 18-24; right column: SEQ ID NOS: 1-2, 25-30, 29, 31, and 32, respectively in order of appearance).

DETAILED DESCRIPTION OF THE INVENTION

Figure 1:
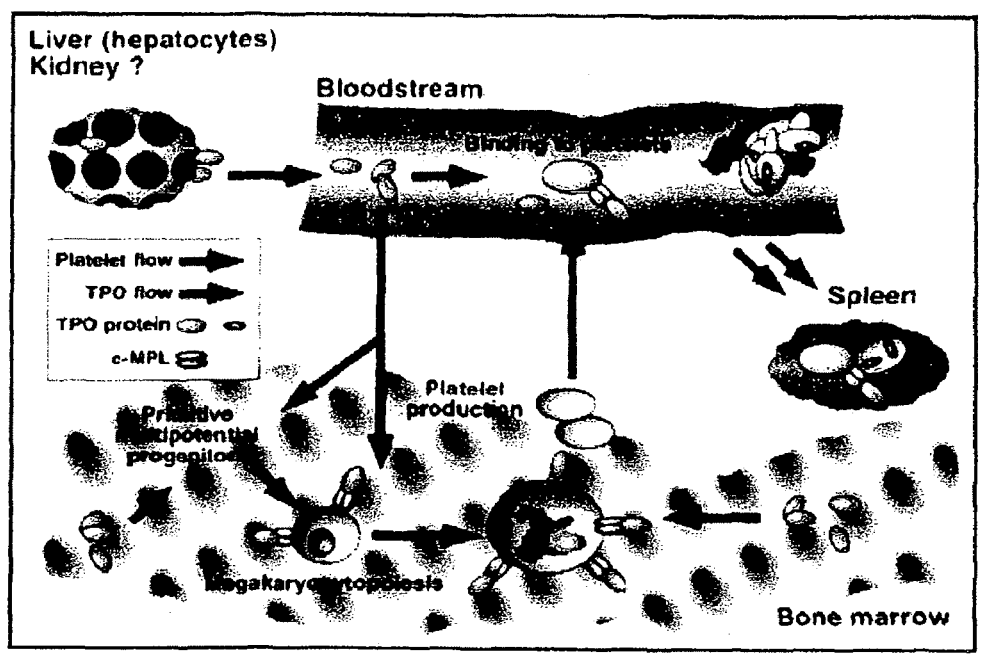
FIG. 1 is a schematic which represents regulation of platelet and HSC production in accordance with the method of the present invention.

The relevant portions of the patent publications and literature cited herein are incorporated by reference herein.

In one embodiment, the present invention is directed to increasing HSC production by administering to a subject a TPO peptide, a TPO mimetic compound, including, but not limited to the compounds set forth in FIG. 2, and PEGylated forms of the compounds set forth in FIG. 2. The methodology that may be employed for PEGylation of the compounds set forth in FIG. 2 is described in U.S. Pat. No. 5,869,451.

In an embodiment, the present invention is directed to increasing HSC production by administering to a subject a TPO peptide, as described in corresponding U.S. application Ser. No. 60/498,740, filed Aug. 28, 2003, the entire contents of which are incorporated herein by reference. According to this embodiment, the TPO peptide is a compound having (1) a molecular weight of less than about 5000 daltons, and (2) a binding affinity to TPO receptor as expressed by an $IC_{50}$ of no more than about 100 μM, wherein from zero to all of the —C(O)NH-linkages of the peptides have been replaced by a linkage selected from the group consisting of —$CH_2OC(O)$NR-linkage; a phosphonate linkage; a —$CH_2S(O)_2$NR-linkage; a $CH_2$NR-linkage; a C(O)$NR^6$ linkage; and a —NHC(O) NH-linkage where R is hydrogen or lower alkyl and $R^6$ is lower alkyl, further wherein the N-terminus of said compound is selected from the group consisting of a —$NRR^1$ group; a —NRC(O)OR group; a —$NRS(O)_2R$ group; a —NHC(O)NHR group; a succinimide group; a benzyloxylcarbonyl-NH group; and a benzyloxycarbonyl-NH group having from 1 to 3 substituents on the phenyl ring selected from the group consisting of lower alkyl, lower alkoxy, chloro and bromo, where R and $R^1$ are independently selected from the group consisting of hydrogen and lower alkyl, and still further when the C-terminus of the compound has the formula —$C(O)R^2$ where $R^2$ is selected from the group consisting of hydroxy, lower alkoxy, and —$NR^3R^4$ where $R^3$ and $R^4$ are independently selected from the group consisting of hydrogen and lower alkyl and where the nitrogen atom of the —$NR^3R^4$ group can optionally be the amine group of the N-terminus of the peptide so as to form a cyclic peptide, and physiologically acceptable salts thereof.

In a related embodiment, the TPO mimetic peptide comprises a sequence of amino acids $X_9X_8GX_1X_2X_3X_4X_5X_6X_7$, where $X_9$ is A, C, E, G, I, L, M, P, R, Q, S, T or V; and $X_8$ is A, C, D, E, K, L, Q, R, S, T or V; and $X_6$ is a β-(2-napthyl) alanine (referred to herein as "2-Nal") residue. More preferably, $X_9$ is A or I, and $X_8$ is D, E or K. Further, $X_1$ is C, L, M, P, Q or V; $X_2$ is F, K, L, N, Q, R, S, T or V; $X_3$ is C, F, I, L, M, R, S, V or W; $X_4$ is any of the 20 genetically coded L-amino acids; $X_5$ is A, D, E, G, K, M, Q, R, S, T, V or Y; and $X_7$ is C, G, I, K, L, M, N, R or V.

A particularly preferred TPO mimetic peptide is I E G P T L R Q (2-Nal) L A A R A (SEQ ID NO: 33).

Another particularly preferred TPO mimetic peptide is I E G P T L R Q (2-Nal) L A A R $X_{10}$, wherein $X_{10}$ is a sarcosine or β-alanine residue or a pegylated form of this compound.

In another embodiment, the TPO mimetic peptide is dimerized or oligomerized to increase the affinity and/or activity of the compound. An example of such a compound includes (SEQ ID NO: 34):

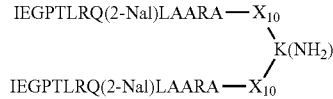

where $X_{10}$ is a sarcosine or β-alanine residue or a pegylated form of this compound. The pegylated form may include a 20 k MPEG residue covalently linked to each N-terminal isoleucine.

According to another embodiment, the TPO mimetic peptide has the following formula:

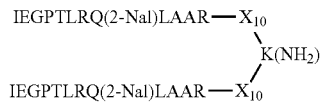

where $X_{10}$ is a sarcosine or β-alanine residue or a pegylated form of this compound. This structure can also be represented by the following structure (H-I E G P T L R Q (2-Nal) L A A R $X_{10})_2$K—$NH_2$. The pegylated form may include a 20 k MPEG residue covalently linked to each N-terminal isoleucine.

One or more TPO mimetic peptides, and in particular PEGylated TPO mimetic peptides (collectively referred to herein as "TPO mimetic compounds" or "TPO mimetic compounds of the invention"), can be used to increase the number of stem cells in bone marrow. Important data supporting the use of a TPO mimetic compound in ASCT is provided by a study performed by Somlo et al., Blood, 93(9):2798-2806 (1999), in which recombinant human thrombopoietin (rhTPO) was able to enhance the mobilization and apheresis yields of CD34+ stem cells in response to G-CSF with consequent reduction in the number of aphereses. Subsequently the engraftment of reinfused cells was also improved in terms of reduced time to ANC>$0.5\times10^9$/L and platelet transfusion independence, though this effect did not reach statistical significance in the small sample size used in this pilot study. By increasing the number of stem cells, the total harvest of stem cells from the subject can be significantly improved. Further, by increasing the number of stem cells harvested from the subject, the number of stem cells available for transplantation back into the subject can also be significantly improved, thereby potentially reducing the time to engraftment (the time during which the subject has insufficient neutrophils and platelets), thus preventing complications.

In addition, the present invention can also reduce the proportion of subjects who are unable to harvest enough cells to proceed with treatment for their primary illness, e.g., chemotherapy and other bone marrow ablative treatments. Furthermore, the proportion of the number of subjects with delayed primary engraftment can also be reduced.

TPO mimetic compounds such as those in FIG. 2 and disclosed herein can be used to increase HSC production. This is accomplished by administering one or more of the compounds to a subject. The compounds set forth in FIG. 2 and disclosed herein, as well as PEGylated forms of the compounds, set forth in FIG. 2 can have reduced immunogenicity relative to one or more of rhTPO and rhIL-11 and can also have an improved pharmacokinetic profile relative to one or more of rhTPO and rhIL-11.

TPO mimetic compounds can also be used to provide autologous HSCs to a subject. Typically, this involves the steps of administering a TPO mimetic compound to a subject in need thereof to enhance expansion of the stem cell population within bone marrow and/or to mobilize the stem cells in peripheral circulation; harvesting one or more of the bone marrow stem cells or one or more of the stem cells in the peripheral circulation; and transplanting the one or more harvested stem cells back into the subject.

In addition, the stem cells obtained from harvesting according to method of the present invention described above can be cryopreserved using techniques known in the art for stem cell cryopreservation. Accordingly, using cryopreservation, the stem cells can be maintained such that once it is determined that a subject is in need of stem cell transplantation, the stem cells can be thawed and transplanted back into the subject.

The TPO mimetic compounds, including the compounds set forth in FIG. 2 and disclosed herein as well as the PEGylated forms of the compounds set forth in FIG. 2, can thus be used for, inter alia: reducing the time to engraftment following reinfusion of stem cells in a subject; reducing the incidence of delayed primary engraftment; reducing the incidence of secondary failure of platelet production; and reducing the time of platelet and/or neutrophil engraftment following reinfusion of stem cells in a subject. These methods typically include the steps of administering a TPO mimetic compound to a subject in need thereof to enhance expansion of the stem cell population within bone marrow and/or mobilize the stem cells in peripheral circulation and then harvesting one or more of the bone marrow stem cells or the stem cells in the peripheral circulation and then transplanting the harvested stem cell back into the subject at the appropriate time, as determined by the particular needs of the subject.

The method of the invention may also be used to increase the number of stem cells from a donor subject whose cells are then used for rescue of a recipient subject who has received bone marrow ablating chemotherapy.

A. Dosage Forms and Routes of Administration

The TPO mimetic compounds useful for the present invention can be administered as pharmaceutical compositions comprising, as an active ingredient, at least one of the peptides or peptide mimetics set forth in FIG. 2 and/or disclosed herein and/or described in U.S. Pat. No. 5,869,451, the entire content of which is hereby incorporated by reference, in association with a pharmaceutical carrier or diluent. The compounds can be administered by oral, pulmonary, parental (intramuscular, intraperitoneal, intravenous (IV) or subcutaneous injection), inhalation (via a fine powder formulation), transdermal, nasal, vaginal, rectal, or sublingual routes of administration and can be formulated in dosage forms appropriate for each route of administration. See, e.g., Bernstein, et al., PCT Patent Publication No. WO 93/25221; Pitt, et al., PCT Patent Publication No. WO 94/17784; and Pitt, et al., European Patent Application 613,683, each of which is incorporated herein by reference.

Solid dosage forms for oral administration include capsules, tablets, pills, powders, and granules. In such solid dosage forms, the active compound can be admixed with at least one inert pharmaceutically acceptable carrier such as sucrose, lactose, or starch. Such dosage forms can also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration include pharmaceutically acceptable emulsions, solutions, suspensions, syrups, with the elixirs containing inert diluents commonly used in the art, such as water. Besides such inert diluents, compositions can also include adjuvants, such as wetting agents, emulsifying and suspending agents, and sweetening, flavoring, and perfuming agents.

Preparations for parental administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Compositions for rectal or vaginal administration are preferably suppositories which may contain, in addition to the active substance, excipients such as cocoa butter or a suppository wax. Compositions for nasal or sublingual administration are also prepared with standard excipients well known in the art.

The compositions of the invention can also be microencapsulated by, for example, the method of Tice and Bibi (in Treatise on Controlled Drug Delivery, ed. A. Kydonieus, Marcel Dekker, New York (1992), pp. 315-339).

The composition can also be combined with, inter alia, G-CSF, SCF, IL-3 or Flt-3 and/or other agents that can enhance stem cell mobilization from bone marrow (including priming chemotherapy and integrin antagonists).

B. Dosage Amount

The quantities of a TPO mimetic compound necessary for the present invention will depend upon many different factors, including means of administration, target site, physiological state of the subject, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman, et al. (eds), Goodman and Gilman's: The Pharmacological Basis of Therapeutics, 8th ed., Pergamon Press (1990); and Remington's Pharmaceutical Sciences, 7th Ed., Mack Publishing Co., Easton, Pa. (1985); each of which is hereby incorporated by reference.

The TPO mimetic compounds are useful for the present invention when administered at a dosage range of from about 0.001 mg to about 20 mg/kg of body weight per day. Alternatively, in some instances 0.0001 mg/kg to about 10 mg/kg may also be administered. The specific dose employed is regulated by the particular condition being treated, the route of administration as well as by the judgement of the attending clinician depending upon factors such as the severity of the condition, the age and general condition of the subject, and the like.

C. Subjects and Indications

As used herein, a subject includes anyone who is a candidate for autologous stem cell or bone marrow transplantation during the course of treatment for malignant disease or as a component of gene therapy. Other possible candidates are subjects who donate stem cells or bone marrow to subjects for allogeneic transplantation for malignant disease or gene therapy.

In order to provide an acceptable probability of engraftment, a minimum number of stem cells must be harvested. Though not precisely defined, it is generally accepted that $2$-$3 \times 10^6$ CD34$^+$ cells per kg must be harvested in order to provide a reasonable chance of engraftment. Reinfusion of $5 \times 10^6$/kg cells appears to produce optimum results in terms of time to engraftment. This large number of cells is required because the actual number of the specific subset of CD34$^+$ cells that are capable of long term reconstitution of bone marrow is very small. As many as 20% of transplanted patients are considered to be poor mobilizers, requiring multiple aphereses to generate sufficient cells. Although one of the most important predictors of poor stem cell mobilization is the age of the patient, heavy pretreatment with chemotherapy is also a significant factor. There are likely a large number of patients, particularly elderly patients with myeloma or NHL, who are not considered for ASCT because of the low probability of successful engraftment.

Consequently the method of the invention provides a solution to the unmet need in ASCT, i.e., the need to improve the proportion of patients who have successful and rapid engraftment. This is achieved primarily due to improvement in mobilization of stem cells, either by increasing numbers of mobilized cells or by increasing the proportion of HSCs in the mobilized CD34+ population. The method of the invention thus provides the following benefits:

1. Allows transplantation to proceed in patients who would not otherwise be considered as candidates because of the unacceptably high risk of failed engraftment;
2. Reduces the number of aphereses required to generate a minimum acceptable harvest;
3. Reduces the incidence of primary and secondary failure of engraftment by increasing the number HSCs available for transplantation; and
4. Reduces the time required for primary engraftment by increasing the number of committed precursors of the important hemopoietic lineages.

In accordance with the established effect of TPO on HSCs, the TPO mimetic compounds of the invention may have the following clinical benefits in stem cell transplantation:

Improvement of apheresis yields: Numerous studies have suggested that the number of reinfused CD34$^+$ stem cells is an important factor in determining the time to engraftment. As demonstrated with TPO, the addition of a TPO mimetic compound may increase mobilization of CD34$^+$ cells as an adjunct to conventional mobilization regimens of G-CSF and chemotherapy. The primary benefit would be to improve the prospect for rapid and subsequent long term engraftment. Reducing the number of aphereses required to generate an acceptable number of cells would reduce cost and patient inconvenience. Improvement in apheresis yields would be of particular benefit in patients with risk factors for low mobilization (age and heavy pretreatment). Such patients may otherwise not be candidates for ASCT.

Improvement of the engraftment potential of apheresed cells: Long term engraftment following myeloablative therapy is produced by a small fraction of the CD34$^+$ cell population (most likely within the CD34$^+$CD38$^-$Lin$^-$ population). Because they are so rare, large numbers of CD34$^+$ cells are required to provide effective engraftment ($2$-$5 \times 10^6$/kg). G-CSF does not affect the proportions of different subtypes of CD34$^+$ cells and is simply used as an agent that can increase the number of these cells in peripheral blood prior to harvest. Priming chemotherapy may actually be toxic to such cells. However TPO is increasingly widely recognized as an agent that can increase the self-renewal of the most primitive stem cells, and thus capable of long-term hemopoietic reconstitution. A similar effect of a TPO mimetic compound may therefore increase the proportion of the CD34$^+$ cell population that can contribute to long-term engraftment and thus reduce the risk of failure of engraftment. TPO may also increase the numbers of stem cells committed to the megakaryocytic lineage thus producing earlier independence from platelet transfusions, i.e., reduced time to engraftment.

The two beneficial effects described above may be additive or synergistic, leading to greater reduction in time to engraftment than might be seen with agents that only increase mobilization of stem cells.

The use of a TPO mimetic compound of the invention would likely require only a small number of doses given, e.g., intravenously or subcutaneously, prior to apheresis. Such a dosing regimen would minimize the risk of significant antigenicity, which is already predicted to be low due to the use of a pegylated product.

The TPO mimetic compound of the invention is first administered to normal volunteers:

1. To establish the effect of the TPO mimetic compound on peripheral blood CD34$^+$ cell populations, platelet counts and other hematological parameters;
2. To establish the preliminary safety profile of the TPO mimetic compound in terms of dose limiting toxicity and high frequency adverse events;
3. To determine the most appropriate dose, dose regimen and dose timing of pre-apheresis dosing with the TPO mimetic compound; and
4. To determine the pharmacokinetic profile of the TPO mimetic compound in humans.

5. To generate preliminary comparative information on the effects of a TPO mimetic compound of the invention and G-CSF on the multilineage potential of peripheral blood stem cells.

Normal human volunteers, which are the most appropriate population for evaluation of pharmacokinetics and initial safety profile, provide the clearest understanding of the effects of the TPO mimetic compound on HSCs because of the absence of the background effects of chemotherapy and disease.

The study will be a single blind, dose rising study in which normal human volunteers receive a single intravenous dose of the TPO mimetic compound of the invention, given as a one hour infusion. The starting dose will be 15 ug/kg. Successive dose cohorts will receive 25, 50, 100 and 200 ug/kg. Four subjects will be enrolled in each cohort, three of whom will receive active therapy and one whom will receive placebo. Each subject will be observed at regular (15 minute) intervals during the infusion and will remain as an inpatient for 24 hours for close safety monitoring and pharmacokinetic sampling. Further outpatient follow up for safety, pharmacokinetic and pharmacodynamic evaluation will occur on days 2, 4, 7, 14, 21 and 28. Each successive dose cohort will be treated two weeks after the previous group.

When a dose is reached at which evidence of pharmacodynamic effect (defined as a 50% increase in platelet count relative to the pretreatment value) is observed in ⅔ of the actively treated subjects dosing at that level will be extended to include a further four subjects (3/1 active/placebo). If the efficacy is confirmed, one further dose cohort of six subjects (4/2 active/placebo) will be enrolled to provide further confirmation of the pharmacodynamic effect. If the pharmacodynamic effect is only observed at the highest planned dose, a further dose increase will be considered, assuming that no evidence of toxicity has been observed.

If a safety/tolerability event that is possibly or probably related to study medication occurs in a single actively treated subject at any dose four further subjects (3/1 active/placebo) will be enrolled at that dose to determine if a dose limiting toxicity has been identified.

Blood samples will be taken for measurement of drug levels 30 minutes after the beginning of the infusion, at the end of the infusion and at the following times after the end of the infusion: 5 minutes, 15 minutes, 30 minutes, 1, 2, 4, 8, 12, 24, 48, 96 hours and 7 and 14, 21 and 28 days. Compound levels will be measured using either a cell based bioassay or by ELISA.

For comparison, a single dose of G-CSF will be administered to three subjects to measure the effects on CD34+ cells.

The effect of the TPO mimetic compound on peripheral blood $CD34^+$ counts, if any will be delayed for several days (3-7 if the effect is similar to thrombopoietin). Furthermore because of the unknown impact of the TPO mimetic compound pharmacokinetics on the PD profile it is not certain when the maximal effect of a single dose will be seen. It is the timing of the maximal effect that will determine the interval between the TPO mimetic compound dosing and harvest of $CD34^+$ cells in subsequent patient studies. A good correlation between peripheral blood $CD34^+$ counts and the yield in subsequent harvesting has been demonstrated suggesting that this approach is reasonable. It may be appropriate to ensure that the TPO mimetic compound invention is given prior to G-CSF to enable an expansion of the HSC population within bone marrow followed by mobilization of the expanded population. Most studies that use G-CSF to stimulate mobilization give the drug for five days with the harvest stated towards the end of the dosing period. It is possible that the pharmacodynamic profile of the TPO mimetic compound will require it to be dosed some days prior to G-CSF.

The impact of the TPO mimetic compound on the number of self-renewing HSCs in the mobilized population could provide an increase in self renewal capacity which could lead to successful engraftment with lower numbers of mobilized cells, greater ease of performing tandem transplants and the possibility that the TPO mimetic compound could eventually replace G-CSF as the standard mobilizing agent.

This aspect of the clinical pharmacology of the TPO mimetic compound can be addressed by measuring the self renewal capacity of $CD34^+$ populations from the normal volunteers study, both in in vitro studies of the ability to sustain long term colony formation (the LTC-IC culture) and by performing SCID/NOD mouse repopulation assays in which the mobilized cells are infused into lethally irradiated SCID/NOD mice. Preliminary calculations indicate that performing such studies should be feasible with the $CD34^+$ cells that are contained in 30-50 mls of blood, provided that the $CD34^+$ count has risen to approximately $15 \times 10^3$/ml.

The assumptions underlying this statement are outlined below:

1. PBMCs from normal subjects will be obtained by Ficoll/Hypaque separation and then Lin+ cells will be removed by negative selection. CD34+CD38− subfractions of this enriched population will then be isolated by FACS and administered to SCID/NOD mice. Mice will also receive accessory cells and growth factors to permit the use of lower numbers of CD34+CD38−Lin− cells per mouse (Bonnet et al., Bone, Marrow Transplantation, 23:203-209 (1999)). Alternatively, the original PBMC population will be used without further purification to provide both repopulating and accessory cells.
2. The primary endpoint for this assay will be survival of the recipient mice. However Southern Blot analyses will also be performed to detect human DNA in the recipient mice. If possible, detection of human progenitor cells will be determined by human selective long term marrow cultures and/or flow cytometry with human specific MAbs.
3. Each subject will provide enough blood to test four CD34+CD38−Lin− cell doses (250, 500, 1000 and 2000 cells/mouse). Each cell dose will be given to 5 mice. With these design assumptions approximately $1.9 \times 10^4$ CD34+CD38−Lin− cells will be needed from each subject. If additional in vitro colony forming studies are performed, more cells will be needed.
4. Each normal subject will provide this blood sample only once and only when the CD34+ cell count in peripheral blood has reached $15 \times 10^3$/ml. CD34+CD38−Lin− population represents 5-8% of CD34+ population (Gallacher et al., Blood, 95:2813-2820 (2000)). Studies with TPO in normal volunteers indicated that $16 \times 10^3$ CD34+ cells/ml were seen in the peripheral blood.
5. 30 mls of blood will be required from each subject to yield $2.25-3.6 \times 10^4$ cells.
6. It will not be possible to perform these studies in placebo treated subjects due to low levels of CD34+ cells ($<3 \times 10^3$/ml). For comparison, similar quantities of cells will be taken from subjects treated with G-CSF. Equal numbers of cells will be infused into the mice.
7. The validity of these assumptions is tested with independent data. Approximately 1 in $6 \times 10^6$ PBMCs is capable of repopulating a SCID/NOD mouse (Wang et al., Blood, 89:3919-3924 (1997)). Of this population, the CD34+ population is 0.13-0.39% and 5-8% of this subset is CD34+CD38−Lin− (Tichelli et al., Br. J. Hematol., 106:152-158 (1999)). This represents 390-1872 cells from the original 6×10⁶ PBMCs. In a separate study the incidence of SCID/NOD repopulating cells in the CD34+CD38−Lin− population has been demonstrated to be 1 in 617 (Bhatia et al., PNAS, 94:5320-5325 (1997)). This number is consistent with the extrapolation to the incidence in unselected cells.

8. If cell number becomes limiting, the highest cell dose cohort of mice will be dropped.

CD34⁺ cells taken from volunteers who are given G-CSF will be used as a control for these studies.

The proposed normal volunteer study will provide the database required to determine the design of patient studies in terms of dose, dose regimen and dose timing as well as strong pharmacodynamic evidence that predicts clinical efficacy. The next phase of the clinical pharmacology program will seek to reproduce the observed effects in patients scheduled for stem cell transplantation as well as providing translational data that will demonstrate a link between the pharmacodynamic endpoints described above and the clinical endpoints required for regulatory approval. The mimetic compound of the present invention is then administered to patients in need:

1. To explore the risk to benefit profile of the TPO mimetic compound in different populations of patients who are candidates for autologous stem cell transplantation; and
2. To obtain preliminary evidence of the likely effect of the TPO mimetic compound on apheresis yields of peripheral blood CD34⁺ stem cells and post engraftment outcomes.

The first patient study will again be a single dose, dose rising design (assuming that there is no reason to give the dose of the TPO mimetic compound as a divided dose). Dosing of the TPO mimetic compound will be introduced into a standard mobilization regimen, with the dose interval between dosing and harvest predicted from the volunteer study. The same pharmacodynamic endpoints will be evaluated in this study as in the previous study, but data on apheresis yields, number of aphereses and subsequent rates and times of engraftment will also be obtained. Dosing will be given via single use 10-20 mg vial containing lyophilized powder as a single dose by intravenous bolus administration before apheresis and after reinfusion of harvested cells. A subcutaneous dosing bioequivalent can be administered with intravenous dosing. It is expected that the dose would be between about 10-300 µg/kg.

A key aspect of this study will be to explore the risk to benefit of the TPO mimetic compound in different patient populations. An increasing number of patients are receiving high dose, myeloablative therapy with ASCT relatively early in the course of their disease. Such patients often have relatively normal bone marrow and, particularly if they are young, are likely to mobilize acceptable numbers of CD34+ cells with consequent high likelihood of rapid engraftment. In this population, the potential impact of an additional agent to enhance mobilization may be limited but could be manifest as even more rapid engraftment with reservation of harvested cells for tandem transplant. Nevertheless, this population, which most closely resembles the normal population at least in terms of bone marrow responsiveness, is an important translational group for the development of the TPO mimetic compound.

Patients who become candidates for ASCT after multiple previous courses of therapy often have greater difficulty in generating enough CD34⁺ cells for an adequate harvest. Consequently, many of these patients require prolonged apheresis schedules and a higher incidence of delayed or failed engraftment. A proportion of these patients are not able to undergo autologous transplant and must instead resort to allogeneic transplant with increased risk of post transplant complications. It is this population in which an additional mobilization agent may be of great benefit.

Consequently, the first patient study will enroll patients from both categories. The data from the 'good mobilizers' will be used as a benchmark to determine the impact of the TPO mimetic compound on the 'poor mobilizers'. A non-treated group, receiving only standard of care will be included.

The pharmacodynamic endpoints outlined above will provide a robust surrogate of the likely clinical benefit of the TPO mimetic compound in ASCT.

Definitive studies will be conducted as parallel group, double blind, placebo controlled studies. Once randomization has occurred clinical decisions about transplantation will be made according to predefined rules and accepted clinical practice.

The primary endpoint for the studies will be mean time to engraftment following re-infusion of harvested cells. Time to engraftment will be defined as number of days until platelet count is maintained above $20 \times 10^9$/L without transfusion support for a period of 7 days.

Secondary endpoints will include:
1. Time to neutrophil engraftment (defined as neutrophil count maintained above $0.5 \times 10^9$/L);
2. Time to platelet count >$50 \times 10^9$/L (maintained for 7 days without transfusion support);
3. Proportion of patients with delayed platelet engraftment;
4. Proportion of patients with secondary failure of platelet engraftment;
5. Proportion of patients who fail to generate minimum harvest necessary for transplantation;
6. CD34⁺ harvest (CD34⁺ cells/kg);
7. Number of aphereses required for harvest; and
8. Number of platelet transfusions.

A key factor in study design will be selection of the target population. Published data indicates that the number of CD34⁺ cells harvested is a major determinant of subsequent engraftment kinetics and will therefore directly impact the primary endpoint of the studies. The key demographic features that will influence the ability to mobilize CD34⁺ cells is the amount of pretreatment and patient age. A number of issues must be considered:

1. If a poor mobilizing population is selected there will be the greatest opportunity to detect an improvement in engraftment rates but the ability of the bone marrow to respond to the TPO mimetic compound may be so compromised that no response is possible;
2. If a high mobilizing population is selected the ability to detect a response over background therapy may be limited due to the fact that optimal numbers of self renewing HSCs will be re-infused regardless of the addition of the TPO mimetic compound;
3. The intrinsic effect of the TPO mimetic compound of the invention to increase mobilization may prevent accurate definition of good or poor mobilizers;
4. The ability to detect the effect on engraftment of an increase in self renewing HSCs may only be seen in patients in whom the number of these cells is a limiting factor in engraftment kinetics.

On the basis of these issues it is important that the study population for these studies is limited in the number of patients at the extremes of the mobilization range. At either extreme it may be difficult to demonstrate the efficacy of the compound. This can be achieved by excluding some patient groups that are highly likely to contribute to extreme values of mobilization (for example patients receiving first line therapy, patients with myelodysplasia and/or low marrow reserve) and also by ensuring that the sample size is determined by patients who reach a predefined range of $CD34^+$ harvest size (i.e., randomized patients who failed to meet these criteria would be replaced).

If a design of this type is followed, the majority of the patients who would contribute to the primary endpoint in the placebo group would have $CD34^+$ yield falling into the following categories in the ratio 2:3:1 respectively:

<$2.0\times10^6$/kg (median time to engraftment=17 days)
2-5$\times10^6$/kg (median time to engraftment=12 days)
>5$\times10^6$/kg. (median time to engraftment=10 days).

In a population of this type, the expected median time to engraftment would be 13-14 days. If the effect of the TPO mimetic compound on yield of $CD34^+$ cells was to alter the proportions of the different harvest categories from 2:3:1 to 1:2:3, this change alone would result in a reduction in the median time to engraftment of 1.66 days. If an improved time to engraftment, within each category caused by increased numbers of self-renewing HSCs, is superimposed on this such that the median time to engraftment improves by 5 days in the lowest yield group (i.e., they behave like the middle yield group) and 2 days in the middle group (i.e., they behave like the high yield group), the additional reduction in median time to engraftment would be 1.66 days. No effect on time to engraftment is assumed for the high yield group. Collectively, the impact of the TPO mimetic compound treatment on median time to platelet engraftment, for the purposes of calculating a sample size, would be 3 days. To enable the maximum opportunity to define the clinical benefit of the TPO mimetic compound a relatively low threshold for the minimum harvest required to allow myeloablation to proceed should be set.

The ability to demonstrate efficacy of the TPO mimetic compound in ASCT is relatively straightforward because the observation of increased numbers of $CD34^+$ stem cell in the peripheral blood of normal volunteers treated with single doses will suffice. The first human study will therefore demonstrate a biologically relevant effect. Several studies have identified the level of $CD34^+$ cells in peripheral blood as an important predictor of subsequent apheresis yield. However the effect on stem cell mobilization in combination with G-CSF will not be established until the first patient study is completed. It will be more difficult to establish that the mobilized $CD34^+$ cells contain increased numbers of stem cells, in part because it is difficult to measure the low levels of HSCs in unstimulated patients. However since G-CSF is reported not to affect the proportion of HSCs in the $CD34^+$ population, it may be possible to infer some effect of the TPO mimetic compound on the number of self renewing HSCs within the mobilized cell population by comparison to cells mobilized with G-CSF.

The most important predictor of success will be apheresis yield. The number of reinfused cells is an important predictor of the subsequent time to engraftment. Consequently the proportion of patients with clinically acceptable or high yields will be a major determinant of the likely impact on time to engraftment and the proportion of patients with delayed or failed engraftment.

It is expected that the TPO mimetic compound is as good as or superior to G-CSF in mobilizing stem cells and that the TPO mimetic compound provides improved quality of the mobilized stem cell population.

A single blind study to evaluate the effect of the TPO mimetic compound on mobilization of peripheral blood CD34+ stem cells when added to standard mobilization regimens in patients scheduled for myeloablative chemotherapy with autologous stem cell transplantation.

To determine the effect of the TPO mimetic compound on the mobilization of stem cells prior to apheresis, a single dose, dose rising study using doses proven to mobilize CD34+ cells in normal volunteers will be conducted. Each dose cohort will contain six patients receiving active medications and two receiving G-CSF background therapy only. Each cohort will be divided into two groups of 3 active and 1 placebo patient. One group will be patients receiving autologous SCT as first line therapy whereas the other will be heavily pretreated patients receiving autologous SCT as salvage therapy. When a dose is reached that produces an increased yield of CD34+ cells relative the placebo patient (effect size to be defined) and to historical controls for the effect of G-CSF on stem cell mobilization, eight additional patients (per subcohort) will be recruited at that dose to solidify the evidence of efficacy and to explore additional pre and post transplant endpoints (to include number of aphereses required to yield $3\times10^6$ cells/kg, the proportion of patients who attain an adequate harvest and the time to post transplantation neutrophil recovery and platelet transfusion independence). Further dose increases will continue as per the original randomization schedule. If one sub-cohort reaches an efficacy plateau or dose limiting toxicity, the remaining sub-cohort will continue in dose escalation. At the time of apheresis, a sample of apheresed cells will be obtained for study of the multipotential capacity of the harvested cells (assuming that the size of the harvest is not limiting). After meeting screening criteria and collection of baseline blood samples, the patient will be receive a single dose of study medication given by intravenous infusion over a period of 60 minutes. Follow up visits will occur every 48 hours until stem cell harvest is complete. Stem cell harvest will be deemed to have failed if 10 aphereses have failed to yield sufficient cells for successful engraftment (minimum $2\times10^6$/kg). The patient will then continue with myeloablative chemotherapy, reinfusion of stem cells, and follow up with appropriate supportive care according to the protocol defined for the patient's tumor. Data on engraftment will be abstracted from the source documents according to predefined specifications.

Samples will be taken for pharmacokinetic sampling at each study visit. Compound levels will be measured using an ELISA.

It is believed that the administration of the TPO mimetic compound in accordance with the method of the invention will provide a number of advantages, including, inter alia:

Reduction in median time to platelet engraftment (defined as platelet count >$20\times10^9$/L) of 3 days when added to standard therapy. Reduction is 1 day when used instead of standard therapy.

Reduction in the proportion of patients with delayed time to platelet engraftment from 40% to 10%.

Increase in the proportion of patients who attain primary platelet recovery (defined as patients who maintain a platelet count >50,000 for 7 days) from 60% to 85%.

Reduction in number of platelet transfusions required (from a median of 5 to a median of 3).

Reduction in median time to ANC>$0.5\times10^9$/L of 1 day.

Reduction in the proportion of patients who fail to meet minimum stem cell harvests ($3\times10^6$/kg) for transplantation (from 35% to 5%) when used in combination with G-CSF.

Increase in the yield of CD34+ cells when used in combination with G-CSF ($4\times10^6$/kg vs $1\times10^6$/kg).

Reduction in the number of harvests required to yield sufficient cells to support transplantation when used in combination with G-CSF (from a median of 3 to a median of 1).

Convenient single dose therapy to improve the efficiency of stem cell transplantation, to permit more aggressive treatment of solid tumors, myeloma and lymphoma and to increase the number of candidates for stem cell transplantation.

Although only particular embodiments of the invention are specifically described above, it will be appreciated that modifications and variations of the invention are possible without departing from the spirit and intended scope of the invention.

What is claimed is:

1. A method of increasing hematopoietic stem cell production in a subject comprising a step of administering a thrombopoietin (TPO) mimetic compound to said subject, wherein the TPO compound has the following sequence:

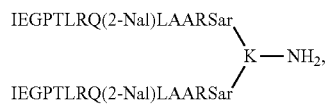

wherein (2-Nal) is β-(2-naphthyl)alanine and Sar is sarcosine.

2. The method of claim 1, wherein the subject is a human.

3. The method of claim 1, wherein the TPO mimetic compound has reduced immunogenicity relative to one or more of the recombinant human thrombopoietin (rhTPO) and recombinant human interleukin-11 (rhIL-11).

4. The method of claim 1 wherein the TPO mimetic compound has an improved PK profile relative to one or more of rhTPO and rhIL-11.

5. The method of claim 1, wherein said TPO mimetic compound is covalently attached to a hydrophilic polymer.

6. The method of claim 5, wherein said hydrophilic polymer has an average molecular weight of between 500 to 40,000 daltons.

7. The method of claim 6, wherein said hydrophilic polymer has an average molecular weight of between 5,000 to 20,000 daltons.

8. The method of claim 6, wherein said hydrophilic polymer has an average molecular weight of 20,000 daltons.

9. The method of claim 5, wherein said polymer is polyethylene glycol.

* * * * *

```
                        SEQUENCE LISTING

<160> NUMBER OF SEQ ID NOS: 34

<210> SEQ ID NO 1
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ile Glu Gly Pro Thr Leu Arg Gln Trp Leu Ala Ala Arg Ala
 1               5                  10

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)
<223> OTHER INFORMATION: Beta-Ala

<400> SEQUENCE: 2

Ile Glu Gly Pro Thr Leu Arg Gln Trp Leu Ala Ala Arg Ala Ala
 1               5                  10                  15

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Ac-Ile
<220> FEATURE:
<221> NAME/KEY: MOD_RES
<222> LOCATION: (3)
<223> OTHER INFORMATION: Sar
<220> FEATURE:
<221> NAME/KEY: MOD_RES
<222> LOCATION: (9)
<223> OTHER INFORMATION: 1-Nal

<400> SEQUENCE: 3

Ile Glu Xaa Pro Thr Leu Arg Gln Xaa Leu Ala Ala Arg Ala
 1               5                  10

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)
<223> OTHER INFORMATION: Ac-Ile
<220> FEATURE:
<221> NAME/KEY: MOD_RES
<222> LOCATION: (3)
<223> OTHER INFORMATION: Sar
<220> FEATURE:
<221> NAME/KEY: MOD_RES
<222> LOCATION: (9)
<223> OTHER INFORMATION: 1-Nal
<220> FEATURE:
<221> NAME/KEY: MOD_RES
<222> LOCATION: (15)
<223> OTHER INFORMATION: Beta-Ala

<400> SEQUENCE: 4

Ile Glu Xaa Pro Thr Leu Arg Gln Xaa Leu Ala Ala Arg Ala Ala
 1               5                  10                  15

<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)
<223> OTHER INFORMATION: Beta-Ala

<400> SEQUENCE: 5

Ile Glu Gly Pro Thr Leu Arg Gln Trp Leu Ala Ala Arg Ala
 1               5                  10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)
<223> OTHER INFORMATION: Ava

<400> SEQUENCE: 6

Ile Glu Gly Pro Thr Leu Arg Gln Trp Leu Xaa Arg
 1               5                  10

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)
<223> OTHER INFORMATION: Ava
<220> FEATURE:
<221> NAME/KEY: MOD_RES
<222> LOCATION: (13)
<223> OTHER INFORMATION: Beta-Ala

<400> SEQUENCE: 7

Ile Glu Gly Pro Thr Leu Arg Gln Trp Leu Xaa Arg Ala
 1               5                  10

<210> SEQ ID NO 8
```

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)
<223> OTHER INFORMATION: N-methyl-Ala

<400> SEQUENCE: 8

Ile Glu Gly Pro Thr Leu Arg Gln Trp Leu Ala Ala Arg Ala
 1               5                  10

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)
<223> OTHER INFORMATION: N-methyl-Ala
<220> FEATURE:
<221> NAME/KEY: MOD_RES
<222> LOCATION: (15)
<223> OTHER INFORMATION: Beta-Ala

<400> SEQUENCE: 9

Ile Glu Gly Pro Thr Leu Arg Gln Trp Leu Ala Ala Arg Ala Ala
 1               5                  10                  15

<210> SEQ ID NO 10
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Ac-Ile
<220> FEATURE:
<221> NAME/KEY: MOD_RES
<222> LOCATION: (14)
<223> OTHER INFORMATION: N-methyl-Ala

<400> SEQUENCE: 10

Ile Glu Gly Pro Thr Leu Arg Gln Trp Leu Ala Ala Arg Ala
 1               5                  10

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Ac-Ile
<220> FEATURE:
<221> NAME/KEY: MOD_RES
<222> LOCATION: (14)
<223> OTHER INFORMATION: N-methyl-Ala
<220> FEATURE:
<221> NAME/KEY: MOD_RES
<222> LOCATION: (15)
<223> OTHER INFORMATION: Beta-Ala
```

```
<400> SEQUENCE: 11

Ile Glu Gly Pro Thr Leu Arg Gln Trp Leu Ala Ala Arg Ala Ala
1               5                   10                  15

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: p-amino-Phe

<400> SEQUENCE: 12

Ile Glu Gly Pro Thr Leu Arg Gln Trp Leu Ala Ala Phe Ala
1               5                   10

<210> SEQ ID NO 13
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: Ac-Lys

<400> SEQUENCE: 13

Ile Glu Gly Pro Thr Leu Arg Gln Trp Leu Ala Ala Lys Ala
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: Ac-Lys
<220> FEATURE:
<221> NAME/KEY: MOD_RES
<222> LOCATION: (13)
<223> OTHER INFORMATION: Ac-Lys

<400> SEQUENCE: 14

Ile Glu Gly Pro Thr Leu Lys Gln Trp Leu Ala Ala Lys Ala
1               5                   10

<210> SEQ ID NO 15
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: 1-Nal
<220> FEATURE:
<221> NAME/KEY: MOD_RES
<222> LOCATION: (14)
<223> OTHER INFORMATION: Beta-Ala
```

```
<400> SEQUENCE: 15

Ile Glu Gly Pro Thr Leu Arg Gln Xaa Leu Ala Ala Arg Ala
 1               5                  10

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)
<223> OTHER INFORMATION: Sar

<400> SEQUENCE: 16

Ile Glu Gly Pro Thr Leu Arg Gln Trp Leu Ala Ala Arg Xaa
 1               5                  10

<210> SEQ ID NO 17
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: 1-Nal
<220> FEATURE:
<221> NAME/KEY: MOD_RES
<222> LOCATION: (14)
<223> OTHER INFORMATION: Sar

<400> SEQUENCE: 17

Ile Glu Gly Pro Thr Leu Arg Gln Xaa Leu Ala Ala Arg Xaa
 1               5                  10

<210> SEQ ID NO 18
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)
<223> OTHER INFORMATION: Beta-Ala

<400> SEQUENCE: 18

Ile Glu Gly Pro Thr Leu Arg Gln Phe Leu Ala Ala Arg Ala
 1               5                  10

<210> SEQ ID NO 19
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: 1-Nal
<220> FEATURE:
<221> NAME/KEY: MOD_RES
<222> LOCATION: (13)
<223> OTHER INFORMATION: Ac-Lys
```

```
<220> FEATURE:
<221> NAME/KEY: MOD_RES
<222> LOCATION: (14)
<223> OTHER INFORMATION: Sar

<400> SEQUENCE: 19

Ile Glu Gly Pro Thr Leu Arg Gln Xaa Leu Ala Ala Lys Xaa
 1               5                  10

<210> SEQ ID NO 20
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: 1-Nal
<220> FEATURE:
<221> NAME/KEY: MOD_RES
<222> LOCATION: (13)
<223> OTHER INFORMATION: Ac-Lys
<220> FEATURE:
<221> NAME/KEY: MOD_RES
<222> LOCATION: (14)
<223> OTHER INFORMATION: Sar

<400> SEQUENCE: 20

Ile Glu Gly Pro Thr Leu Arg Glu Xaa Leu Ala Ala Lys Xaa
 1               5                  10

<210> SEQ ID NO 21
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: 1-Nal
<220> FEATURE:
<221> NAME/KEY: MOD_RES
<222> LOCATION: (13)
<223> OTHER INFORMATION: Ac-Lys
<220> FEATURE:
<221> NAME/KEY: MOD_RES
<222> LOCATION: (14)
<223> OTHER INFORMATION: Sar

<400> SEQUENCE: 21

Ile Glu Gly Pro Thr Leu Ala Gln Xaa Leu Ala Ala Lys Xaa
 1               5                  10

<210> SEQ ID NO 22
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: 1-Nal
<220> FEATURE:
<221> NAME/KEY: MOD_RES
<222> LOCATION: (13)
<223> OTHER INFORMATION: Ac-Lys
<220> FEATURE:
<221> NAME/KEY: MOD_RES
```

```
<222> LOCATION: (14)
<223> OTHER INFORMATION: Sar

<400> SEQUENCE: 22

Ile Glu Gly Pro Thr Leu Ala Glu Xaa Leu Ala Ala Lys Xaa
 1               5                  10

<210> SEQ ID NO 23
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: 1-Nal
<220> FEATURE:
<221> NAME/KEY: MOD_RES
<222> LOCATION: (13)
<223> OTHER INFORMATION: Nle
<220> FEATURE:
<221> NAME/KEY: MOD_RES
<222> LOCATION: (14)
<223> OTHER INFORMATION: Sar

<400> SEQUENCE: 23

Ile Glu Gly Pro Thr Leu Arg Gln Xaa Leu Ala Ala Xaa Xaa
 1               5                  10

<210> SEQ ID NO 24
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: Nle
<220> FEATURE:
<221> NAME/KEY: MOD_RES
<222> LOCATION: (9)
<223> OTHER INFORMATION: 1-Nal
<220> FEATURE:
<221> NAME/KEY: MOD_RES
<222> LOCATION: (13)
<223> OTHER INFORMATION: Nle
<220> FEATURE:
<221> NAME/KEY: MOD_RES
<222> LOCATION: (14)
<223> OTHER INFORMATION: Sar

<400> SEQUENCE: 24

Ile Glu Gly Pro Thr Leu Xaa Gln Xaa Leu Ala Ala Xaa Xaa
 1               5                  10

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)
<223> OTHER INFORMATION: Abu
<220> FEATURE:
<221> NAME/KEY: MOD_RES
<222> LOCATION: (12)
<223> OTHER INFORMATION: DipheAla
```

```
<400> SEQUENCE: 25

Ile Glu Gly Pro Thr Leu Arg Gln Trp Leu Xaa Xaa
 1               5                   10

<210> SEQ ID NO 26
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)
<223> OTHER INFORMATION: Abu
<220> FEATURE:
<221> NAME/KEY: MOD_RES
<222> LOCATION: (12)
<223> OTHER INFORMATION: Diphe
<220> FEATURE:
<221> NAME/KEY: MOD_RES
<222> LOCATION: (13)
<223> OTHER INFORMATION: Beta-Ala

<400> SEQUENCE: 26

Ile Glu Gly Pro Thr Leu Arg Gln Trp Leu Xaa Xaa Ala
 1               5                   10

<210> SEQ ID NO 27
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)
<223> OTHER INFORMATION: Abu
<220> FEATURE:
<221> NAME/KEY: MOD_RES
<222> LOCATION: (12)
<223> OTHER INFORMATION: DipheAla

<400> SEQUENCE: 27

Ile Glu Gly Pro Thr Leu Arg Gln Trp Leu Xaa Xaa Arg
 1               5                   10

<210> SEQ ID NO 28
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)
<223> OTHER INFORMATION: Abu
<220> FEATURE:
<221> NAME/KEY: MOD_RES
<222> LOCATION: (12)
<223> OTHER INFORMATION: Diphe
<220> FEATURE:
<221> NAME/KEY: MOD_RES
<222> LOCATION: (14)
<223> OTHER INFORMATION: Beta-Ala

<400> SEQUENCE: 28

Ile Glu Gly Pro Thr Leu Arg Gln Trp Leu Xaa Xaa Arg Ala
 1               5                   10
```

```
<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)
<223> OTHER INFORMATION: Abu
<220> FEATURE:
<221> NAME/KEY: MOD_RES
<222> LOCATION: (12)
<223> OTHER INFORMATION: DipheAla

<400> SEQUENCE: 29

Ala Asp Gly Pro Thr Leu Arg Glu Trp Ile Xaa Xaa
 1               5                  10

<210> SEQ ID NO 30
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)
<223> OTHER INFORMATION: Abu
<220> FEATURE:
<221> NAME/KEY: MOD_RES
<222> LOCATION: (12)
<223> OTHER INFORMATION: DipheAla
<220> FEATURE:
<221> NAME/KEY: MOD_RES
<222> LOCATION: (13)
<223> OTHER INFORMATION: Beta-Ala

<400> SEQUENCE: 30

Ala Asp Gly Pro Thr Leu Arg Glu Trp Ile Xaa Xaa Ala
 1               5                  10

<210> SEQ ID NO 31
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: Ava

<400> SEQUENCE: 31

Ala Asp Gly Pro Thr Leu Arg Glu Trp Ile Ser Phe Xaa Ala Asp Gly
 1               5                  10                  15

Pro Thr Leu Arg Glu Trp Ile Ser Phe
             20                  25

<210> SEQ ID NO 32
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32
```

```
Cys Ile Glu Gly Pro Thr Leu Arg Gln Trp Leu Ala Ala Arg Ala
 1               5                  10                  15

<210> SEQ ID NO 33
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: 2-Nal

<400> SEQUENCE: 33

Ile Glu Gly Pro Thr Leu Arg Gln Xaa Leu Ala Ala Arg Ala
 1               5                  10

<210> SEQ ID NO 34
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: 2-Nal
<220> FEATURE:
<221> NAME/KEY: MOD_RES
<222> LOCATION: (15)
<223> OTHER INFORMATION: Sar, Beta-Ala, or not present

<400> SEQUENCE: 34

Ile Glu Gly Pro Thr Leu Arg Gln Xaa Leu Ala Ala Arg Ala Xaa
 1               5                  10                  15
```